(12) United States Patent
Knopf et al.

(10) Patent No.: US 8,474,304 B2
(45) Date of Patent: Jul. 2, 2013

(54) DEVICE FOR THE DETERMINATION OF THE CONCENTRATION OF SOLID PARTICLES

(75) Inventors: Franz Knopf, Graz (AT); Helmut Pongratz, Graz (AT); Alexander Bergmann, Graz (AT)

(73) Assignee: AVL List GmbH, Graz (AT)

( * ) Notice: Subject to any disclaimer, the term of this patent is extended or adjusted under 35 U.S.C. 154(b) by 676 days.

(21) Appl. No.: 12/654,945

(22) Filed: Jan. 8, 2010

(65) Prior Publication Data

US 2010/0175459 A1 Jul. 15, 2010

(30) Foreign Application Priority Data

Jan. 13, 2009 (AT) .................................. 14/2009 U

(51) Int. Cl.
*G01N 1/22* (2006.01)
(52) U.S. Cl.
USPC ........................................................ 73/28.04
(58) Field of Classification Search
USPC ........................ 73/28.01, 28.04, 23.31, 118.1
See application file for complete search history.

(56) References Cited

U.S. PATENT DOCUMENTS

| 5,058,440 | A | * | 10/1991 | Graze, Jr. .................. 73/863.83 |
| 6,796,165 | B2 | | 9/2004 | Abdul-Khalek |
| 7,549,350 | B2 | | 6/2009 | Graze |
| 7,610,793 | B2 | * | 11/2009 | Liu et al. ...................... 73/28.01 |
| 7,647,810 | B2 | * | 1/2010 | Wei et al. ...................... 73/23.31 |
| 2007/0131038 | A1 | * | 6/2007 | Wei et al. ...................... 73/865.5 |
| 2008/0148870 | A1 | | 6/2008 | Wei et al. |
| 2009/0049934 | A1 | | 2/2009 | Bergmann et al. |

FOREIGN PATENT DOCUMENTS

JP 2006226893 8/2006

OTHER PUBLICATIONS

English Abstract of JP2006226893.

* cited by examiner

*Primary Examiner* — Daniel Larkin
(74) *Attorney, Agent, or Firm* — Dykema Gossett PLLC

(57) ABSTRACT

A device for determination of solid particle concentration includes a primary diluter (6), a downstream heated evaporator (7), a secondary diluter (8) downstream of the evaporator (7) and a particle counter (5). The secondary diluter (8) is a porous tube diluter and is mounted between the outlet of the evaporator (7) and a stabilization chamber (14), from which the sample flow is diverted to the particle counter (5).

7 Claims, 3 Drawing Sheets

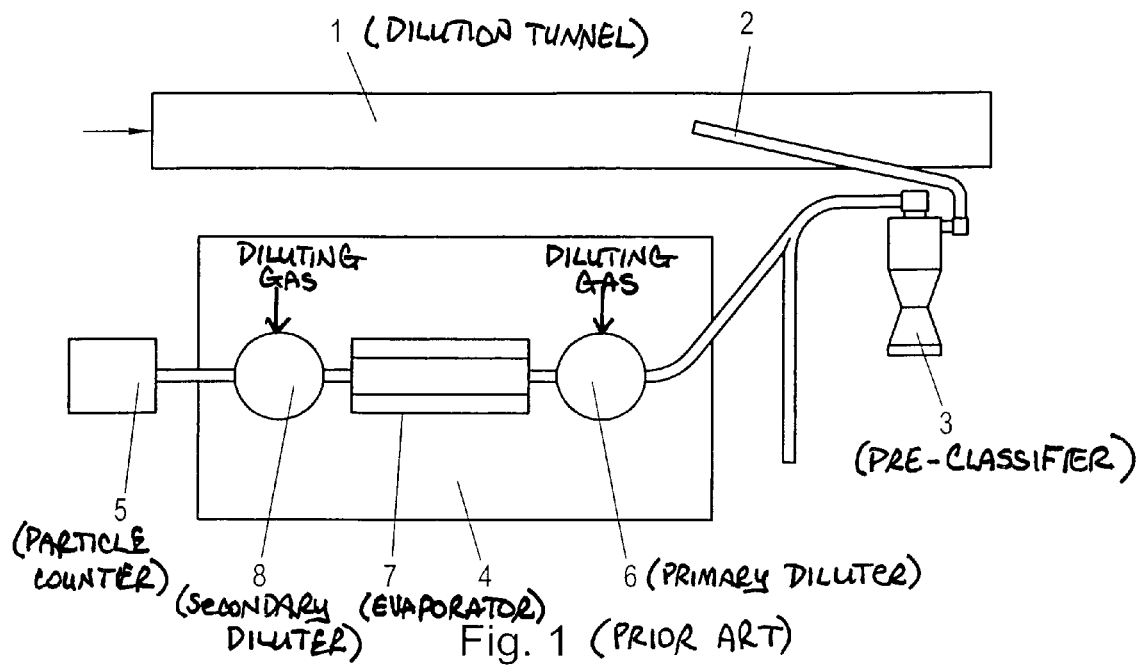
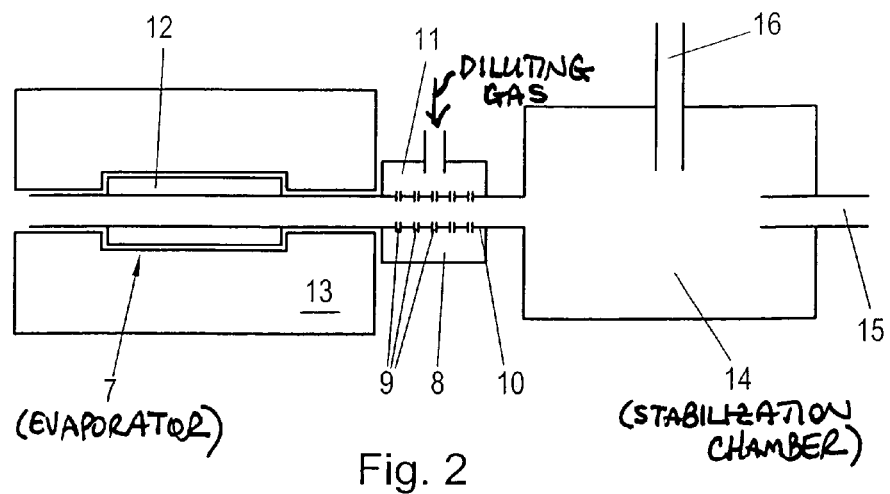

DEVICE FOR THE DETERMINATION OF THE CONCENTRATION OF SOLID PARTICLES

BACKGROUND OF THE INVENTION

1. Field of the Invention

The invention concerns a device for determining the concentration of solid particles in a particle-loaded gas stream with a pre-diluter mixing a sample flow branched off from the gas stream with a substantially particle-free diluting gas, a heated evaporator downstream in the diluted sample flow, a secondary diluter downstream of the evaporator and mixing the sample flow with additional substantially particle-free diluting gas, and a particle counter downstream of the secondary diluter.

2. The Prior Art

Devices of the type mentioned and the processes performed with such are known particularly in connection with the characterization and measurements of aerosols in the exhaust gas of combustion engines and are at least partially also already the subject matter of national as well as regional and international test regulations, standards and the like. A relatively detailed description of a device of the type mentioned is contained, for example, in the "Amendments to UNECE regulations/regulation Number 83/Appendix 5" (United Nations, Economical and Social Council, Economic Commission for Europe; January 2008). Further, some devices are also already available commercially that contain these suggested elements and thus make corresponding measurements possible.

As is known, exhaust gases of combustion engines and particularly those of diesel engines contain not only classic aerosols (within the meaning of volatile suspended particles), but a mixture of solid and volatile suspended particles in a carrier gas, whereby the harmfulness of the corresponding analyses of the exhaust gases is almost exclusively caused by the solid particles. Devices of the type mentioned at the beginning that are of interest here therefore aim to eliminate the volatile particles that are not relevant for the definition of harmfulness prior to the final measurement, for which purpose the sample flow is sequentially diluted, heated and diluted again. In the pre-diluter that can, for example, be designed as per AT 9.603 U, the concentration of solid particles as well as of volatile aerosols is decreased in the sample flow. In the downstream heated evaporator, the volatile substances are transformed into the steam phase, whereby as a result of adjusting a corresponding pre-dilution, the concentration of volatile aerosols can be reduced to the extent that the steam pressure of these substances subsequent to the evaporator is so low that they no longer condensate even during subsequent cooling, as a result of which the sample stream that is to be cooled again subsequently then only still contains the solid particles that are to be counted.

To make the measurement or counting of the solid particles that are of interest possible in a wide range of the actual particle concentration in the particle-loaded gas stream, particularly the interplay of the dilution rate in the pre-diluter and secondary diluter, as well as the various states of heating and cooling of the sample flow must be able to be coordinated precisely or be controllable, which makes the specific executions of commercial systems that correspond to the recommendations of the UNECE regulations discussed at the beginning very complex, as a result of which they, for example, are scarcely used for test stands of local motor vehicle departments, auto repair shops and the like.

It is the problem of the present invention to design or improve a device of the type described at the beginning so that for a wide range of measurements a simple adjustment and control becomes possible.

According to the present invention, this problem is solved by a device of the type described at the beginning thereby, that the secondary diluter is designed as a porous tube diluter and mounted between an outlet of the evaporator and a stabilization chamber from which the sample flow is diverted to the particle counter. A porous tube diluter of this type is provided with—at least on a part of the sample line running through it—circumferential openings, which flow from the outside, subject to at least slight over pressure, supplying substantially particle-free diluting gas to the sample line and can mix there with the sample flow in a manner that can be adjusted or controlled easily. As a result, the desired cooling of the sample flow also takes place directly, whereby it is ensured in the manner described previously that the volatile aerosol particles that evaporated during the prior heating cannot condensate again. As the result of the controllable dilution of the secondary diluter, together with the controllable dilution of the pre-diluter and the heating temperatures or cooling temperatures of the sample flow, a very wide range of the solid particles that are of interest can be covered in the final analysis in the concentrations that are to be measured in the downstream particle counter.

In a preferred embodiment of the invention, the secondary diluter is connected with the heated evaporator by a thermally isolated sample line, which ensures that heat exchange from the sample gas stream to the tube wall is prevented, and thus thermophoretic deposits of the aerosol particles can be avoided.

The secondary diluter that is designed as a porous tube diluter is preferably provided with a large number, preferably >1,000 circumferential openings in the sample line, preferably having a diameter of <0.15 mm, to which the additional diluting gas can be supplied as preferably a thermally controllable cold dilution stream from a sealed casing space that surrounds the sample line in this section in a sealed manner. As a result, a controlled secondary dilution and cooling of the sample flow takes place that is controlled extending over a relatively large circumferential section and very many mixing points.

In a further embodiment of the invention, the circumferential openings of the secondary diluter can also be designed tapered with a cross section that decreases from the outside toward the inside and further, also in the radial and/or axial direction deviating from the normal, aligned with the respective line surface, which results in further advantageous possibilities of influencing the mixture and thus dilution and cooling.

In a preferred embodiment of the invention, the stabilization chamber that is downstream of the secondary diluter is designed with a significantly larger cross section with respect to the sample line in the secondary diluter and has, in addition to an exhaust opening, at least one sampling connection for the particle counter. As a result of the thus present significant change of the Reynolds number at the transition into the stabilization chamber, a homogeneous mixture is formed with the diluting gas supplied in the secondary diluter, whereby representative samples can then be removed from the stabilization chamber, which are measured in the particle counter (for example, a known condensation counter) for the determination of the concentration of the remaining solid particles.

In the following, the invention is explained in more detail with the aid of the examples of embodiments that are illustrated schematically in the drawings.

BRIEF DESCRIPTION OF THE DRAWINGS

FIG. 1 shows the schematic illustration of a particle sampling system that is recommended as per UNECE Regulation Number 83-Appendix 5, with the essential components of the device according to the invention FIG. 2 shows a schematic illustration of an evaporator, secondary diluter and stabilization chamber according to the present invention;

DETAILED DESCRIPTION OF THE PREFERRED EMBODIMENT

Figure 2A:
FIG. 2a shows a detail of FIG. 2 with the circumferential openings in the sample line between the stabilization chamber and the evaporator of FIG. 3 extending radially and with decreasing cross-sections.

The device according to FIG. 1 is used for the determination of the concentration of solid particles in a particle-loaded gas stream that is supplied here by the supplier of the gas stream in a manner that is not shown in greater detail—for example, of a diesel combustion engine—a dilution tunnel (CVS tunnel) 1 and is mixed there and stabilized with filtered and temperature controlled and humidity controlled dilution air. A sample flow that is diverted from tunnel 1 by a diverter tube 2 to a pre-classifier 3, which represents a pre-selection with respect to particle size, to a unit 4 that has the task of removing the volatile aerosols from the sample flow or transform such into the steam phase so that a downstream particle counter 5 only still measures the actually interesting solid particles or their concentration in the sample flow.

In unit 4, the sample flow that is supplied by pre-classifier 3 first arrives in a pre-diluter 6, in which—in a manner that is not shown here—substantially particle-free dilution gas is mixed in controllably. This pre-diluter can, for example, be designed as a rotary diluter, such as described, for example, in AT 9.603 U. A heated evaporator 7 is located downstream of the pre-diluter 6, which permits heating of the diluted sample flow to approximately 350° C.-400° C. A secondary diluter 8 is located downstream of evaporator 7, by means of which a further dilution and cooling of the sample stream that is now free of volatile aerosols as a consequence of pre-dilution and heating, which is then conveyed to particle counter 5.

According to FIG. 2, as per the invention, the secondary diluter 8 is designed as porous tube diluter and has a large number (preferably more than 1,000) of circumferential openings 9 in sample line 10, of which here, for reasons of clarity only a few are shown in enlargement. These circumferential openings 9 are supplied with the additional dilution gas as preferably a temperature controlled cold dilution flow from the sealed casing space 11 that surrounds the sample line 10 in this section, which insures a thorough mixing and cooling of the heated sample stream that was heated in the section of the heated evaporator 7. The secondary diluter 8 is connected with the heated evaporator 7 by a section of the thermally insulated sample line 10 that is as short as possible, so that deposits of the aerosol particles can be avoided in this section. The heating unit of the evaporator is labeled 12 and the insulation is labeled 13.

The circumferential openings 9 at sample line 10 in secondary diluter 8 are preferably provided with a diameter of <0.15 mm and can also be designed to be tampered with a cross-section that decreases from the outside toward the inside (see FIG. 2a)—further, as the result of an alignment that deviates from a normal with respect to the line surface of these circumferential openings, an additional influence on the inflow behavior of the additional dilution gas is possible and thus on the thorough mixing and cooling of the gas flow.

The downstream stabilization chamber 14 is designed with a significantly larger cross section with respect to the sample line 10 in secondary diluter 8, as a result of which a significant change of the Reynolds number occurs at the transition to a further homogenous mixing of the sample flow with the diluting air. In addition to an exhaust opening 15, a sampling connection 16 is provided laterally, by means of which representative samples for one or also for several measuring devices, particularly particle counters, can be removed.

Figure 3:
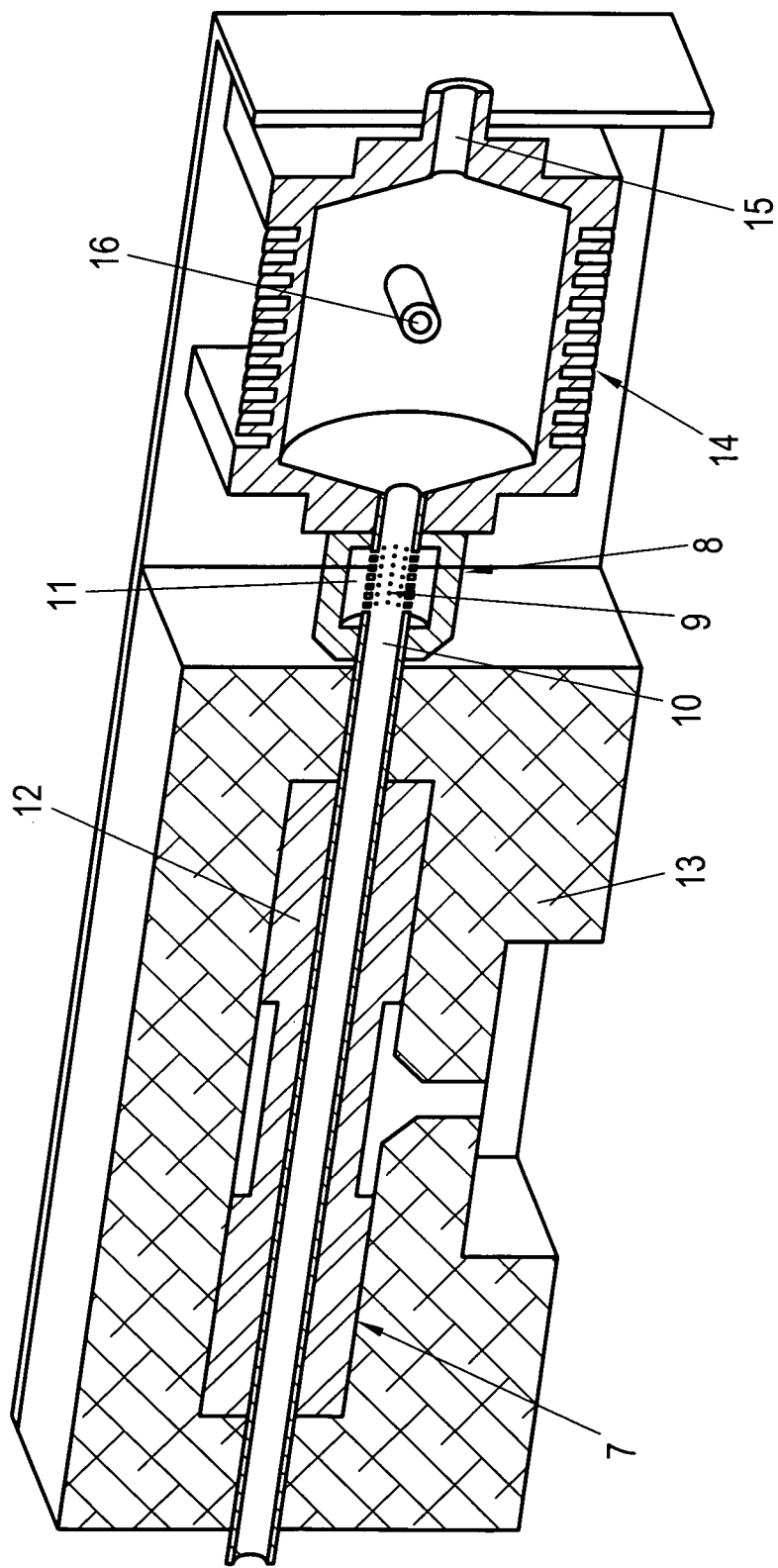
FIG. 3 shows the partial unit as per FIG. 2 as a cross-section of the specific device.

In the specific embodiment shown in cross-section in FIG. 3, functional elements that correspond to FIG. 2 have been provided with the same reference numbers. The description of FIG. 2 also applies to FIG. 3, unchanged.

The invention claimed is:

1. A device for the determination of the concentration of solid particles in a particle-loaded gas stream, comprising:
    a primary diluter for mixing a sample flow diverted from the gas stream with a substantially particle-free diluting gas,
    a heated evaporator downstream of the primary diluter,
    a secondary diluter downstream of the heated evaporator for mixing the sample flow with additional substantially particle-free diluting gas, said secondary diluter being connected to the heated evaporator by a thermally insulated sample line and comprising a porous tube mounted between the evaporator and a stabilization chamber, and
    a particle counter downstream of the secondary diluter.

2. The device according to claim 1, wherein the insulated sample line of the secondary diluter includes a plurality of circumferential openings and means forming a sealed casing space surrounding said sample line and said circumferential openings for supplying said additional diluting gas thereto.

3. The device according to claim 2, wherein circumferential openings are tapered with a decreasing cross section in a radially inward direction.

4. The device according to claim 2, wherein the secondary diluter includes at least 1,000 circumferential openings.

5. The device according to claim 2, wherein the additional dilution gas is a thermally adjustable cold dilution stream.

6. The device according to claim 2, wherein said circumferential openings extend in an axial, non-radial direction.

7. The device according to claim 1, wherein the stabilization chamber has a larger cross-section than a cross-section of the sample line in the secondary diluter, and includes at least one sampling connection for the particle counter in addition to an exhaust opening.

* * * * *